United States Patent [19]

Gill

[11] Patent Number: 4,569,767
[45] Date of Patent: Feb. 11, 1986

[54] RECLAMATION PROCESS FOR SEWAGE SCUM

[76] Inventor: Jagroop S. Gill, 8080 - 113B St., Delta, British Columbia, Canada, 4VC 5E8

[21] Appl. No.: 591,426

[22] Filed: Mar. 20, 1984

[51] Int. Cl.[4] ............................................. C02F 11/18
[52] U.S. Cl. .................................. 210/718; 210/737; 210/768
[58] Field of Search ............... 210/608, 707, 710, 718, 210/737, 768–771, 774, 799, 800

[56] References Cited

U.S. PATENT DOCUMENTS 3,652,405  3/1972  Hess et al. ........................... 210/608
4,248,709  2/1981  Irving ............................... 210/771 X

*Primary Examiner*—Thomas Wyse
*Attorney, Agent, or Firm*—Seed and Berry

[57] ABSTRACT

This invention relates to recovery of fatty acids from sewage scum and the subsequent upgrading of the fatty acids as a processed oil through vacuum distillation and deodorization.

5 Claims, No Drawings

RECLAMATION PROCESS FOR SEWAGE SCUM

DESCRIPTION

This invention relates to a process of recovery, purification and utilization of brown sewage scum or skimmings in the form of a semi-solid mixture which are formed during processing of municipal sewage by conventional techniques. These skimmings have heretofore been a nuisance waste. The sewage scum or skimmings are first recovered from the municipal waste by conventional skimming techniques. The raw scum is then heated by injecting steam through the scum at 75 to 100 psi for 3 to 4 hours. At 65° C. or above, the semi-solid mixture is fluidized by the heat of the steam and hydrolized to a free fatty acid mixture comprising fatty acids having from about 3 to 24 carbon atoms, such as butyric acid, caproic acid, stearic acid, oleic acid, palmitic acid, etc.

The hydrolyzed mixture is pumped into a mechanical vibrator which employs a series of screens sized to remove any solid matter from the mixture. From there it proceeds through a two-stage macroscopic solid filter which removes finely comminuted solids.

The filtered mixture is then placed in a settling tank for 1 to 2 days. The tank temperature of the settling tank is maintained by injection into the filtered mixture of stripping steam at about 75 psi to sterilize the mixture and reduce the concentration of low molecular weight fatty acids in the mixture, such as butyric acid.

In the settling tank, the fatty acid component or oil layer of the mixture rises to the top of the tank, and a waxy interphase forms between the oil layer and the water layer. Water and the interphase are drawn from the bottom of the tank.

The oil phase from the top of the settling tank is pumped to storage and solidifies on cooling. The oil phase contains more than 70% of a mixture of fatty acids, principally acids such as stearic, oleic and palmitic acids. The processed oil fraction may also be further upgraded by vacuum distillation to fully deodorize it.

The foul-smelling, low molecular weight compounds, such as butyric acid, are removed in a forerun fraction during the vacuum distillation, allowing isolation of a clean fraction consisting of identifiable fatty acids, principally stearic, oleic and palmitic acids. The fatty acid mixture may be blended with wood waste, and the blended mixture formed into fuel logs.

I claim:
1. A process for recovering a fatty acid-containing fraction from sewage scum of municipal sewage plants, comprising:
   (1) heating the sewage scum containing the fatty acid-containing fraction to a temperature sufficient to liquefy the scum,
   (2) introducing sufficient steam into the fatty acid-containing fraction to hydrolyze the fraction to form a free fatty acid mixture,
   (3) removing entrained water and solids from the liquefied mixture, and
   (4) cooling the liquefied mixture to obtain a solidified product mixture containing about 70% fatty acids.
2. The process of claim 1 wherein the fatty acids contain from about 3 to 24 carbon atoms.
3. The process of claim 2, including, after step (2), feeding the liquefied mixture into a settling tank, maintaining the temperature of the mixture in the settling tank by injection of steam sufficient to retain the fatty acid mixture in liquefied form while allowing a waxy component of the mixture to solidify, and separating the liquefied fatty acid mixture from the waxy component and any water.
4. The process of claim 3, including subjecting the fatty acid mixture to vacuum distillation for removal of foul-smelling, low molecular weight fatty acids from the remainder of the fatty acid mixture, and recovering a fatty acid fraction consisting essentially of the higher molecular weight fatty acids.
5. The process of claim 1, including blending the fatty acid mixture with wood waste and forming the blended mixture into fuel logs.

* * * * *